United States Patent [19]

Scott

[11] Patent Number: 4,555,936
[45] Date of Patent: Dec. 3, 1985

[54] MULTIFUNCTIONAL DETECTOR

[75] Inventor: Raymond P. W. Scott, Wilton, Conn.

[73] Assignee: The Perkin-Elmer Corporation, Norwalk, Conn.

[21] Appl. No.: 685,009

[22] Filed: Dec. 13, 1984

Related U.S. Application Data

[63] Continuation-in-part of Ser. No. 555,182, Nov. 23, 1983.

[51] Int. Cl.⁴ .............................................. G01N 31/08
[52] U.S. Cl. .................................... 73/61.1 C; 356/436
[58] Field of Search ...................... 73/61.1 C; 324/450; 356/436; 250/461.1; 422/58, 70; 436/161

[56] References Cited

U.S. PATENT DOCUMENTS

| | | | |
|---|---|---|---|
| 2,709,781 | 5/1955 | Douty et al. | 324/450 |
| 3,920,334 | 11/1975 | Steichen et al. | 250/461.1 X |
| 3,941,487 | 3/1976 | Ehret et al. | 73/61.1 C X |
| 4,233,030 | 11/1980 | Twitchett et al. | 73/61.1 C X |
| 4,462,962 | 7/1984 | Baba et al. | 422/58 |

Primary Examiner—Stewart J. Levy
Assistant Examiner—Joseph W. Roskos
Attorney, Agent, or Firm—E. T. Grimes; F. L. Masselle; J. D. Crane

[57] ABSTRACT

A detector assembly includes means for determining the fluorescence characteristics, the ultraviolet absorbance characteristics and the electrical conductivity characteristics of a single sample of an eluate of a chromatographic separating column.

16 Claims, 4 Drawing Figures

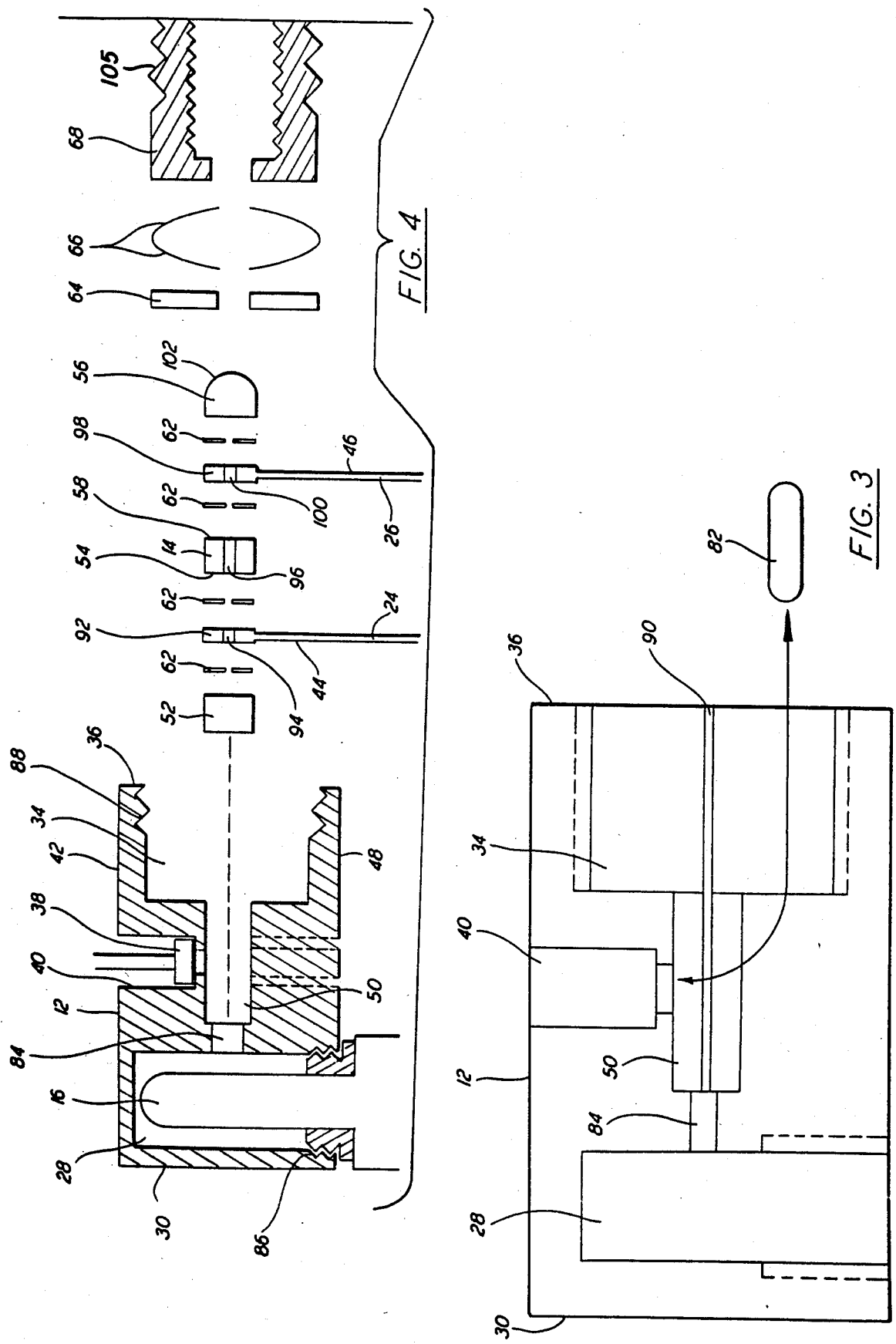

MULTIFUNCTIONAL DETECTOR

BACKGROUND OF THE INVENTION

This application is a continuation-in-part of application Ser. No. 555,182, filed Nov. 23, 1983.

The present invention generally relates to a detector especially useful in liquid chromatography and, in particular, relates to a detector having multiple detection functions.

In liquid chromatography, a sample solution is passed through a separating column which is designed to partition the sample into its constituents such that the constituents are serially eluted. The eluent of the column is analyzed to characterize the constituents as they elute.

Generally, the characterization of liquid chromatography eluents is performed by determining the absorption, the fluorescence or the conductivity properties of the eluent. Presently, each of these properties requires a different discrete detector mechanism. For example, to measure light absorption, the detector mechanism must direct radiation through the eluate and detect that amount of radiation which passes therethrough. To measure fluorescence, the detector must include a source of radiation to initiate the fluorescence and a sensor, usually positioned at a right angle to the initiating radiation, for receiving the fluorescence. The measurement of the conductivity of an eluate requires at least two spaced apart electrodes in contact with the eluent.

Due to the inherent physical configurations and component requirements, conventional liquid chromatography detectors measure only one of the above properties. Hence, in order to investigate more than a single property of an eluate it has been necessary to either arrange multiple detectors in series or perform multiple separations with the same sample but with different detectors.

In the first approach, i.e., the use of multiple detectors in series, the major factor inherently present which reduces the accuracy and reliability of the results is that the band dispersion of the eluate is always increased as it is passed through each detector.

The major difficulty in exploring the second approach is, or course, the time and expense required to perform the identical separation two, three or more different times.

SUMMARY OF THE INVENTION

Accordingly, it is one object of the present invention to provide a detector useful in liquid chromatography which can detect a plurality of properties of an eluate.

This object is accomplished, at least in part, by a housing block having at least two different property characterization elements operatively associated with a single sample cell therein.

Other objects and advantages will become apparent to those skilled in the art from the following detailed description read in conjunction with the appended claims and the drawing attached hereto.

BRIEF DESCRIPTION OF THE DRAWING

The drawing, not drawn to scale, includes:

FIG. 3—which is a front view of a housing block for use in the detector shown in FIG. 1; and FIG. 4—which is an assembly view of the detector shown in FIG. 1.

DETAILED DESCRIPTION OF THE INVENTION

Figure 1:
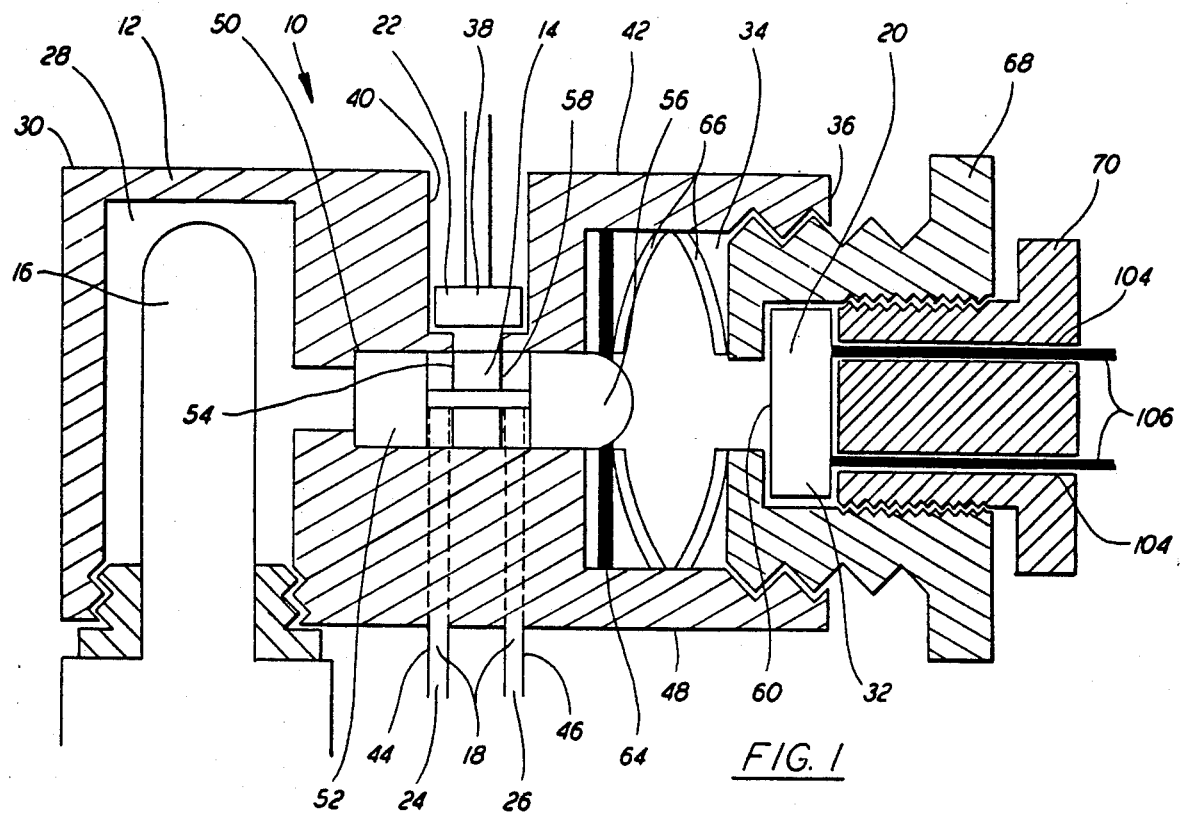
FIG. 1—which is a cross-sectional view of a detector embodying the principles of the present invention.

A detector assembly, generally indicated at 10 in the drawing and embodying the principles of the present invention, includes a housing block 12 having a sample cell 14 defined therein. The detector assembly 10 also includes a source of radiation 16, means 18 for measuring the electrical conductivity of a liquid passing through the sample cell 14, means 20 for detecting radiation passing through the sample cell 14, and means 22 for detecting fluorescence radiation occurring within the sample cell 14. The detector assembly 10 is also provided with sample inlet and outlet conduits, 24 and 26, respectively, for passing a sample fluid through the sample cell 14.

In a preferred embodiment, the detector assembly 10 includes the source of light radiation 16 in a first opening 28 near one end 30 of the housing block 12, a first photodetector 32 disposed inwardly of the other end 36 of the block 12, a second photodetector 38 in a third opening 40 in one sidewall 42 of the block 12, and first and second spaced apart electrodes, 44 and 46 respectively, extending through a second sidewall 48 of the block 12 and adapted to be contacted by liquid passing through the sample cell 14.

In addition, the housing block 12 includes a bore 50 therein for receiving the sample cell 14 and having a first optical window 52 at one end 54 of the sample cell 14 and a second optical window 56 at the other end 58 of the sample cell 14. Preferably, the second optical window 56 is shaped to disperse light passing therethrough from the sample cell 14 over more of the surface 60 of the first photodetector 32.

In the preferred embodiment, the first and second electrodes, 44 and 46 respectively, are hollow and serve as the inlet and outlet conduits, 24 and 26 respectively, and each is sandwiched between a pair of seals 62 which form a fluid tight seal about the ends of the sample cell 14 as well as electrically isolate the electrodes, 44 and 46.

As shown in FIG. 1, the second optical window 56 is securely positioned by means of a retaining washer 64 which is urged against the second window 56 by a pair of spring washers 66 held in place via a lens retaining nut 68. The first photodetector 32 is fixedly positioned within the lens retaining nut 68 by means of a detector retaining nut 70. In this fashion the spacing between the second optical window 56 and the first photodetector 32 remains constant. As a consequence, the detector measurement characteristics of the first photodetector 32, i.e., which primarily depends upon both the spacing between the second window 56 and the surface 60 of the photodetector 32 and the specific surface area of the photodetector used, remains constant for a given photodetector.

The detector assembly 10 is clearly advantageous since any one of a plurality of properties can be measured without interchanging the detector. Additionally, since more than one property can be measured simultaneously, all properties are measured on exactly the same sample.

Figure 2:
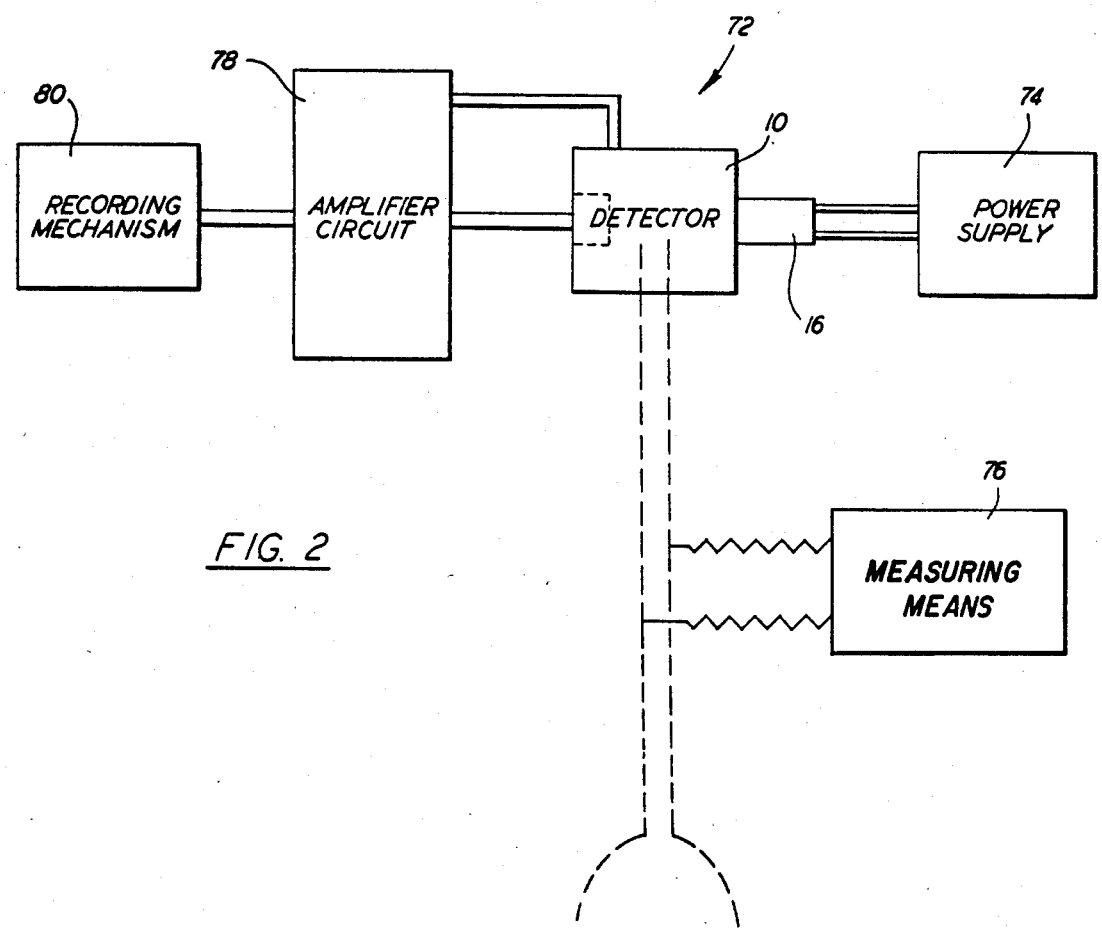
FIG. 2—which is a block diagram of a detector system employing a detector embodying the principles of the present invention.

A system, generally indicated at 72 in FIG. 2 and specifically adapted to function with the detector assembly 10, for measuring a plurality of properties includes a high voltage power supply 74 for energizing the source of light radiation 16 thereof. The first and second electrodes, 44 and 46 respectively, are connected to a measuring circuit 76 which, in the preferred embodiment, includes a Wheatstone bridge type circuit for accurately measuring the impedance between the electrodes, 44 and 46.

The first and second photodetectors, 32 and 38 respectively, of the detector assembly 10 are electrically connected to a signal amplifier circuit 78 which provides a representative output signal to a recording mechanism 80. Preferably, the recording mechanism 80 includes, as at least one mode thereof, a strip chart recorder for providing a chromatogram.

Another major advantage of the detector assembly 10 is the ease by which it can be fabricated and assembled. This advantage is more fully discussed hereinafter with respect to a specific embodiment shown in FIGS. 3 and 4.

A 2.5 cm by 2.5 cm by 3 cm long housing block 12 of opaque chemically resistant material, such as, for example, Delrin®, a registered trademark of the duPont Corporation, is initially machined as shown in FIG. 3. Specifically, the lamp receiving first opening 28 is formed with a diameter of about 8 mm and axially located about 6 mm from the one end 30 of the block 12. A 3 mm × 1.5 mm slot 82 is formed in the third opening 40 and opens into the bore 50 which passes through the center of the block 12. Preferably, the bore 50 is about 4.5 mm in diameter. A 2 mm long internal opening 84 of about 3 mm diameter is formed between the bore 50 and the first opening 28 to form a passage through which light radiation passes into the bore 50. The third opening 40, having a diameter of about 1 cm, is formed in the one sidewall 42 generally symmetrical about the slot 82. Preferably, the third opening 40 is axially perpendicular to the bore 50. This is sized to receive the second photodetector 38, i.e., which measures the fluorescence radiation.

A second opening 34, for receiving the lens retaining nut 68 and the first photodetector 32 is formed in the block 12 from the other end 36 to a depth of about 8 mm. Preferably, the first opening 28 is provided with an internal thread 86, for example, ⅜-24 threads per inch, and the second opening 34 is provided with internal threads 88, for example, ½-20 threads per inch. In order to simplify the final assembly of the electrically conductive inlet and outlet conduits 24 and 26, respectively, a 0.8 mm slot 90 is formed in the block 12 from the other end 36 and extends thereinto to the end of the bore 50, i.e., a distance on the order of about 1.9 cm.

Referring now more specifically to FIG. 4, the final assembly of the detector assembly 10 is more fully discussed hereinafter.

As shown, the first optical window 52, in the form of a flat surfaced quartz lens, is inserted into the bore 50 from the other end 36 of the block 12. Adjacent that lens is a 0.125 mm thick polytetrafluroethelene (PTFE) seal 62 followed by the mobile phase inlet conduit 24. As an alternative, the seals 62 can also be formed from other chemically resistant materials such as that known as KAPTON®, a registered trademark of duPont Corporation. The mobile phase inlet conduit 24 includes a washer-like end 92 having a 0.75 mm diameter opening 94 therethrough. A second PTFE seal 62 is inserted and thereafter the sample cell 14 is inserted adjacent the second seal 62. Preferably, the sample cell 14 is a glass disk having an outside diameter of about 4.5 mm and an opening 96 therethrough which is 0.75 mm diameter by 2 mm long. For reasons well known in the art, such a sample cell 14 introduces very little band dispersion and is a relatively low volume cell. Thereafter, a third PTFE seal 62 and the mobile phase outlet conduit 26, also having a washer-like end 98 and an opening 100 therethrough, are inserted and followed by a fourth PTFE seal 62. This arrangement completely seals the bore 50 and prevents fluid leakage through the slot 90. Further, this assembly 10 seals the electrodes, 44 and 46, and prevents sample leakage thereabout. Finally, the second window 56, preferably having a concave surface 102 distal the light source 16, is inserted and retained in place by retaining washer 64. In order to secure, and more exactly position the second window 56 with respect to the first photodetector 32, the second window 64, and hence the assembly within the bore 50, is retained in place by the pair of opposing spring washers 66 biased inwardly by means of the lens retaining thread 105 which mates with the internal thread 88 of the second opening 34.

In one particular embodiment, the sample cell 14 is opaque to the radiated light, with the consequence that light is only passed through the opening 96 into the cell 14, but transparent to the fluorescent radiation. For example, if the source of radiation 16 transmits in the approximate wavelength band of 180 nm to 280 nm and the fluorescent radiation of interest is greater than about 350 nm, such as the conditions when characterizing quinine sulfate, a borosilicate glass could be used for the sample cell 14. Of course, other light sources, such as, for example, light emitting diodes, infrared, could also be used with a corresponding selection of material for the sample cell 14.

Referring back to FIG. 1, the first photodetector 32 is then secured within the lens retaining nut 68 by means of a detector retaining nut 70 having openings 104 therethrough for the electrical leads 106 thereof to be connected to the amplifier circuit 78 external the block 12. In the preferred embodiment, the electrically conductive inlet and outlet conduits, 24 and 26 respectively, are formed from stainless steel tubing having an inside diameter of about 0.25 mm and an outside diameter on the order of about 0.5 mm. The washer-like disk is provided at the ends thereof to not only ensure electrical contact between the conductive conduits, 24 and 26, and the fluid flowing therethrough, but also provides a surface against which the seals 62 can create a fluid tight seal for both the sample cell 14 and the electrodes 44 and 46.

The detector assembly 10 described herein not only provides the chromatographic advantages of low volume and low dispersion, but additionally provides major advantages in the selection and characterization of an eluate from a liquid chromatography separating column. As will be understood from the previous discussion relating to the system 72, shown in FIG. 2, any one of three properties can be measured either individually, in pairs or all three simultaneously. Such availability of measuring possibilities on the identical amount of sample fluid provides reliable determinations and characterizations of eluents from separating columns.

In designing a trifunctional detector of the type disclosed, there are numerous considerations, some of which interact with each other, that must be accounted for in the final design. Ideally, the sample cell should be small in volume and preferably less than 3 $\mu$L although larger sized cells will function but not as efficiently. The cell must be sufficiently long to provide an adequate signal according to Beer's Law. As a consequence of these two criteria, the cross-sectional area of the cell must be very small. In order that the radiation intensity is sufficient to be detected as intensity is controlled by the inverse square of the distance, the radiation source must be located as close as possible to the face of the cell. It also follows for this reason that the radiation sensor should be as close as possible to the other face of the cell. As the cross-sectional area of the radiation passing through the sample is small, it is desirable to have a divergent lens to distribute the radiation passing through the sample over the surface of the radiation sensor.

In order for the trifunctional detector to be able to measure sample conductivity, the electrodes must be sufficiently far apart so as to permit conductivity measurement. The sample cell and the rest of the detector must also be made in a manner so that the electrodes are electrically isolated from each other. Also, since conductivity must be measured over the length of the sample cell, the electrodes must be designed so that they do not interfere with the radiation passing through the sample.

The cell of the trifunctional detector must also be designed so that its walls are transparent to florescent light from the sample therein. The fluorescence sensor must be located as close as possible to the cell to avoid loss of sensitivity. It is also desirable to be able to locate a filter between the cell and the fluorescence sensor to filter the incident radiation and transmit the flourescent radiation.

The detector must be designed in a manner permitting disassembly thereof to permit cleaning of the parts. When assembled, however, the detector must have a liquid tight seal at the typical pressure of a liquid chromatograph.

The present invention has been described herein in relationship to a particular specific embodiment which embodiment is exemplary only as other assemblies and configurations will become apparent to those skilled in the art from reading this description. Hence, the present invention is deemed limited only by the appended claims and the reasonable interpretation thereof.

What is claimed is:

1. A detector for determining a plurality of characteristics of a liquid sample, the detector comprising, in combination:
a housing block;
an elongated sample cell with a central bore disposed along an axis and positioned within said block through which a liquid can flow, said cell having two opposite ends;
means for determining the electrical conductivity of a liquid within said cell, said conductivity determining means including electrodes disposed adjacent said opposite ends of said elongated sample cell;
a source of radiation disposal within said block at one end of said cell for directing radiation through the liquid in said cell in a direction generally parallel said axis;
a radiation sensor disposed within said block at the opposite end of said cell for detecting the level of the radiation from said source after passing through the liquid in said cell;
a fluorescence sensor means disposed in said block so that fluorescence radiation from the liquid in said sample cell impinges thereon but radiation from said radiation source does not impinge thereon.

2. The detector as claimed in claim 1 further comprising:
an inlet conduit at one end of said sample cell for introducing said liquid sample into said cell, and
an outlet conduit at the other end of said sample cell for removing said liquid sample from said sample cell.

3. The detector as claimed in claim 2 wherein said inlet and said outlet conduits are electrically isolated and define said electrodes of said conductivity determining means.

4. The detector as claimed in claim 1 further comprising:
means for sealing said sample cell, said means having openings therethrough whereby radiation can pass through both ends of said sample cell.

5. The detector as claimed in claim 1 further comprising:
means, positioned between said sample cell and said first photosensor, for optically expanding the cross-section of radiation passing through said sample cell prior to said radiation impinging upon said first photosensor.

6. A detector for determining a plurality of characteristics of a liquid sample, the detector comprising, in combination:
an elongated housing block with two opposite faces;
a first opening near one face of said housing block;
an elongated central bore passing through one said face and communicating with said first opening;
a second opening in said block communicating with said central bore at a point intermediate opposite ends of said bore;
a radiation source disposed within said first opening for producing a radiation which passes through said bore;
an elongated substantially cylindrical cell made of an electrically insulative and fluorescence radiation transparent material, said cell having a central passage therethrough and an axis through said central passage, said cell being disposed in said central bore so that radiation from said radiation source passes through said central passage;
a radiation sensor disposed in said bore at a position where radiation passing through said cell from said source impinges thereon;
electrically conductive means disposed adjacent opposite ends of said cell and within said bore, said electrically conductive means being shaped to contact any liquid in said cell while permitting radiation to pass from said source to said detector;
optical window means disposed adjacent opposite ends of said cell permitting radiation from said source to pass therethrough;
two conduit means each coupled to one of the two opposite ends of said cell to provide a path so that liquid can be passed through said cell;
a plurality of sealing means for providing a liquid tight path between one said conduit and said other conduit, said sealing means being shaped to permit radiation from said source to pass through said cell and impinge on said detector;
a fluorescence sensor disposed in said second opening and disposed so that fluorescence radiation from inside said cell can impinge thereon while radiation from said source does not impinge thereon.

7. The detector of claim 6 wherein said block is made of an insulative material.

8. The detector of claim 6 wherein said central passage has a volume of not substantially more than 3 micro liters.

9. The detector of claim 6 wherein said window adjacent said radiation sensor comprises a divergent lens to direct the radiation passing though said cell substantially onto the entire surface of said radiation sensor.

10. The detector of claim 6 wherein said electrically conductive means are each in the shape of an anulus with a central opening through which said radiation passes.

11. The detector of claim 10 wherein each said conduit means is made of an electrically conductive material and each said conduit contacts one said conductive means.

12. A detector for determining a plurality of characteristics of a separated liquid sample from the column of a liquid chromatograph comprising, in combination:
an elongated substantially cylindrical cell with an axis made of an electrically insulative and flourescence radiation transparent material, said cell having a central passage therethrough;
a first and second electrically conductive means disposed adjacent opposite ends of said cell, each having a bore therethrough communicating with and substantially the size of said central passage, said first and second conductive means comprising two spaced electrodes between which a liquid is located thereby permitting measurement of the liquid conductivity;
optical window means disposed adjacent each said electrically conductive means;
a plurality of liquid tight seals disposed between said cell and each said conductive means and between each said window means and each said conductive means adjacent thereto;
means for introducing liquid from said liquid chromatograph column through said first conductive means into the bore therethrough in a direction generally perpendicular to the axis of said cell;
means for removing liquid from said bore of said second conductive means;
a radiation source disposed adjacent one said optical window for directing radiation through one said window, along the length of said cell and out through said other window;
a radiation detector disposed to intercept the radiation exiting from said other window for measuring the light transmission characteristics of the liquid in said cell;
a flourescence detector for detecting flourescence radiation from said cell and positioned so that radiation from said source does not impinge thereon;
said cylindrical cell being selected to have a large enough diameter so that radiation impinging on said radiation detector produces a usable signal compared to the noise signal produced by said radiation detector when no radiation impinges thereon and small enough that separated band dispersion is not adversely affected;
said cylindrical cell having a length sufficient enough to assure radiation absorption occurs in said cell and yet sufficiently short to minimize separated band dispersion within said cell;
said cylindrical cell being large enough in diameter to assure sufficient flourescence radiation impinges on said flourescence detector to be detected thereby and sufficiently small so as to minimize separated band dispersion within the cell; and
said means for introducing liquid being operative to break up the parabolic velocity profile within said cell to reduce separated band dispersion within the cell.

13. The detector of claim 12 wherein said cylindrical cell has a volume of about 3 micro liters.

14. The detector of claim 12 wherein said cylindrical cell has an inner diameter of about 0.75 mm. and a length of about 3 mm.

15. The detector of claim 12 wherein said optical window disposed closest said radiation detector comprises a divergent lens for distributing radiation passing therethrough evenly over the surface of said radiation detector.

16. The detector of claim 12 wherein said means for introducing liquid and said means for removing liquid are made of an electrically conductive material.

* * * * *